United States Patent [19]
de Radzitzky d'Ostrowick et al.

[11] 4,038,322
[45] July 26, 1977

[54] PROCESS FOR THE OXIDATION OF PARAFFINS

[76] Inventors: Pierre M. J. G. de Radzitzky d'Ostrowick, 101 Avenue Paul Hymans, Woluwe-St-Lambert, Brussels; Jacques D. V. Hanotier, 36 Avenue Docteur Decroly-uccle., Brussels 18; Joseph M. E. Vaerman, 28 Clos Fernand Tonnet, Jette-Brussels 9, all of Belgium

[21] Appl. No.: 655,997

[22] Filed: Feb. 6, 1976

Related U.S. Application Data

[62] Division of Ser. No. 239,367, March 29, 1972, abandoned, which is a division of Ser. No. 844,616, , Pat. No. 3,758,557.

[51] Int. Cl.$^2$ ............................................. C07C 45/02
[52] U.S. Cl. .......................... 260/597 R; 260/488 R; 260/632 R

[58] Field of Search .......... 260/597 R, 488 R, 632 R, 260/586 P

[56] References Cited
U.S. PATENT DOCUMENTS

| | | | |
|---|---|---|---|
| 2,223,495 | 12/1940 | Lodar | 260/586 P |
| 2,265,948 | 12/1941 | Lodar | 260/597 R |
| 2,659,746 | 11/1953 | Morgan et al. | 260/597 R |
| 2,969,380 | 1/1961 | Selwitz | 260/597 R |

Primary Examiner—Bernard Helfin
Assistant Examiner—James H. Reamer
Attorney, Agent, or Firm—S. B. Wiczer

[57] ABSTRACT

Straight-chain paraffins are nondestructively and selectively oxidized to introduce oxy and oxo functions predominantly at the 2 position by an oxidizing system comprising a compound of group II – VI metals in higher valent form and an acidic activator of dissociation constant greater than $5.10^{-3}$ or boron trifluoride, with or without molecular oxygen and with or without a solvent.

7 Claims, No Drawings

PROCESS FOR THE OXIDATION OF PARAFFINS

This is a division of application Ser. No. 239,367 filed Mar. 29, 1972, now abandoned, which is in turn a division of Ser. No. 844,616, now U.S. Pat. No. 3,758,557.

This invention relates to a process for the selective oxidation of straight-chain paraffins into oxygenated products having the same number of carbon atoms, specifically into alcohols, mainly in the form of esters, or into ketones, in which the oxygenated function is preferentially situated in the 2-position of the carbon chain.

The straight-chain paraffins are the least reactive hydrocarbons. When a paraffin of this type is attacked chemically, it is observed that the two terminal methyl groups have a greater resistance than the internal methylene groups and that these are attacked in statistical manner. In his book *Chemie und Technologie der Paraffin-Kohlenwasserstoffe*, F. Asinger clearly shows that the attack on a straight-chain paraffin by chlorination, nitration sulphochlorination, sulphoxidation and oxidation by oxygen in the liquid phase extends in statistical manner to the aggregate of the methylene groups of the chain.

With respect to the formation of oxygenated compounds in particular, most of the prior works relate to the oxidation of straight-chain paraffins in the liquid phase by molecular oxygen, most frequently in the presence of a catalyst based on manganese, such as potassium permanganate. This method has been applied on an industrial scale for the production of fatty acids. The selectivity of such observed oxidations is poor, however, since a great number of other oxygenated products are formed at the same time, such as alcohols, esters, aldehydes, ketones, ethers, peroxides and hydroperoxides. Since the reaction is also accompanied by substantial degradation of the hydrocarbon chain, an extremely complex mixture of oxygenated products is obtained whose separation and purification is protracted and costly.

It has now been found according to this invention that the straight-chain paraffins may be catalytically oxidized at low temperature to selectively attack the second carbon atom of the chain in a consistently advantageous manner. By an appropriate choice of the operating conditions, the oxidation is effected selectively and non-destructively to secure preferential production of alcohols (mainly in the form of esters) or of ketones having the same number of carbon atoms as the original paraffin. The oxidizing system hereof comprises a compound of a metal of variable valency and an activator of acid nature.

The main object of the present invention is to provide a process for oxidation at low temperature of straight-chain paraffins into oxygenated products having the same number of carbon atoms, in which the oxygenated function is preferentially situated at the 2 position of the carbon chain, with preferential formation of alcohols, mainly in the form of esters, or alternatively with preferential formation of ketones.

According to the present invention a process for the selective oxidation of straight-chain paraffins into oxygenated compounds having the same number of carbon atoms, comprises oxidizing a straight-chain paraffin in the liquid phase with an oxidizing system comprising a compound of a metal of variable valency, the metal being in the higher valency state and having an oxidation-reduction potential of at least 0.99 volt, and an activator selected from the group consisting of acids having a dissociation constant greater that $5 \times 10^{-3}$ and which are stable under the conditions of the reaction, boron trifluoride, and mixtures thereof, at a temperature in the range of $-20°$ C to $-100°$ C.

It is useful but not essential to employ a solvent for the reaction to form the liquid phase reaction medium. In particular cases, the oxidizing system is soluble in the paraffin to be oxidized and the reaction may occur in the solution thus obtained. Most frequently, however, the reactants should be dissolved, at least partially, in a common solvent. To this end, it is possible to employ any liquid reasonably stable to oxidation by the oxidizing system and in which the latter and the paraffin to be oxidized are sufficiently soluble. The lower fatty acids, that is to say those which have 2, 3 or 4 atoms of carbon, as well as their lower esters of an aliphatic alcohol having 1 to 4 carbon atoms, in particular their methyl and t-butyl esters, satisfactorily fulfil the preceding conditions. Among these solvents, acetic acid is particularly advantageous.

Normally the compounds of metals of variable valency which can be employed are those in which the multi-valent metal is a group II, III, IV, V or VI metal, used at its higher valency and which has an oxidation-reduction potential of at least 0.99 volt, for example, cobalt (III), cerium (IV), Vanadium (V), Chromium (VI), silver (II) and lead (IV). Of these metals, cobalt (III) is preferred since it results in a particularly high proportion of products oxidized at position 2 in the carbon chain. It also is best for preferential conversion of the paraffins into alcohols, mainly in the form of esters, or into ketones, depending on the conditions of reaction which have been selected.

Among the compounds of these metals, the salts of carboxylic acids have the advantage of usually being soluble in organic media and particularly cobalt (III) salts of carboxylic acids are soluble and preferred herein. Any sufficiently soluble cobaltic carboxylate can be employed; the cobaltic salts of the lower fatty acids having 2, 3 or 4 carbon atoms of carbon, are particularly advantageous, since they are easily produced from the corresponding cobalt (II) salts. For example, cobaltic acetate can be obtained by co-oxidation of cobalt (II) acetate with acetaldehyde in acetic acid in the presence of oxygen as is disclosed in U.S. Pat. No. 1,976,757. The cobaltic salts of the other fatty acids may be produced in analogous manner or by interchange reaction between such other carboxylic acids and cobaltic acetate.

A fundamental and important feature of the present invention is the discovery that the oxidizing capacity of these metal compounds, and more specifically of these cobaltic salts, in respect of straight-chain paraffins, is increased considerably by the presence of a relatively strong inorganic or organic acid. As a general rule, the acids which can fulfil this activating function are those which have a dissociation constant K higher than $5 \times 10^{-3}$. Such strong acids should also be substantially soluble in the reaction medium and should not interfere with the reaction. Useful strong acids herein are sulphuric acid ($K_1 > 1$), perchloric acid ($K > 1$), p-toluenesulphonic acid ($K > 1$), trifluoroacetic acid ($K = 6 \times 10^{-1}$), Trichloroacetic acid ($K = 2 \times 10^{-1}$), dichloroacetic acid ($K = 3.3 \times 10^{-2}$) and phosphoric acid ($K = 7.5 \times 10^{-3}$). Some Lewis acids, for example boron trifluoride, also have an activating action. It is also possible to employ a mixture of these acids. Acids which tend to further modify the oxidation products such as the hydrohalogen acids, such as HCl, or nitric acid are usually avoided.

The activating action of the acids defined hereinabove influence the rate of the reaction as well as its degree of advance. It is the more pronounced the more strong the acid and to a particular limit, the higher its concentration. On the other hand, the quantity of acid to be employed depends on the nature as well as on the quantity of the metal compound employed. For example, if sulphuric acid is employed to activate a cobaltic salt, it is preferred to have a molecular ratio between the acid and salt of approximately 2, to secure a maximum of activity. A ratio between 5 and 20 is preferable with a weaker acid, like trifluoracetic acid. Although the mechanism of the activation has not yet been clarified, the facts indicate that the cobaltic salt and the acid interact to form a more oxidation active species which would be principally responsible for the initial attack on the hydrocarbon. For example, the following theoretical mechanism in which the cobaltic salt, the acid and the active species, are represented respectively by $Co^{3+}$, AH and Co(III) is useful to explain $$AH \rightleftharpoons A^- + H^+ \qquad (1)$$
$$Co^{3+} + H^+ > Co\,(III) \qquad (2)$$

The nature of the oxidation products which can be obtained by the process of the invention is determined in particular by the composition of the oxidizing system. For example, if the metal component of this system is chromic anhydride, ketones form the principal products of the reaction. With lead (IV) oxide, alcohols will be obtained more easily, principally in the form of esters. The nature of the products with other compounds, and specifically with cobaltic compounds depends essentially on the operating conditions. Thus, to produce esters, the reaction should be performed in a carboxylic acid solvent such as acetic acid, and in the absence of free oxygen. For example, in these conditions n-heptane can be converted almost quantitatively into heptyl acetates with a considerable proportion of 2-heptyl acetate. The esters thus obtained may then be hydrolysed to produce alcohols, or pyrolised to produce olefins. To obtain ketones however, the operation should be conducted in the same medium and in the presence of oxygen with vigorous stirring of the reaction mixture. In these conditions, n-heptane is oxidized primarily into heptanones, again with a considerable proportion of 2-heptanone. These particular examples clearly demonstrate the extraordinary selectivity of the process and the high degree of control made available by simple selection of the experimental conditions.

The medhanism of the reactions resulting in these different products, is not known with certainty. The action of oxygen set forth hereinabove, however suggests that the primary attack on the paraffin results in the formation of a free radical (reaction 3) capable of reacting with molecular oxygen (reaction 4) to produce a peroxy radical which would then be converted to form a ketone. In the absence of oxygen, the radical would be oxidized in its turn, probably whilst forming a "carbonium" salt (reaction 5) which, in the presence of a carboxylic acid, would lead to an ester (reaction 6)

$$RH + Co(III) \rightarrow R^- + Co^{2+} + H^+ \qquad (3)$$
$$R^- + O_2 \rightarrow ROO. \rightarrow ketone \qquad (4)$$
$$R^- + Co(III) \rightarrow R^+ + Co^{2+} \qquad (5)$$
$$R^+ + R'COOH \rightarrow ROCOR' + H^+ \qquad (6)$$

According to this reaction scheme, the proportion of ketones and of esters in the reaction products would be the result of competition between the reactions (4) and (5). It can then be seen that to promote the production of esters, it is necessary to choose conditions which prevent the reaction (4), that is to say operating in the absence of molecular oxygen. By contrast, to promote the production of ketones, it is necessary to choose conditions allowing the reaction (4) to predominate, that is to say operating in the presence of a gaseous phase containing oxygen and assuring vigorous stirring for rapid diffusion of the latter into the liquid phase.

This gaseous phase may consist of pure oxygen or of a mixture of oxygen with other gases inert in the conditions of the reaction; air may be employed, for example. The partial oxygen pressure may lie between 0.1 and 50 atmospheres. In particular cases, it is possible to apply pressure outside this range. For example, a lower pressure than 0.1 atmosphere is sufficient at times— subject to the condition of ensuring particularly effective stirring. On the other hand, pressures higher than 50 atmospheres may be applied, but these do not result in an improvement in the results such as to justify additional plant investment. In the majority of cases, an oxygen pressure of 1 to 10 atomspheres may advantageously be applied to secure a high proportion of ketones.

The high degree of activity of the oxidizing system applied in the present invention renders it possible to oxidize the paraffins at low temperature, more specifically within a temperature range of from $-20°$ to $100°$ C. in practice, the choice of temperature will be dictated by the nature of the oxydizing system and by the effect of the temperature on the rate and selectivity of the reaction. As a general rule, the rate of reaction increases with the temperature while its selectivity tends to decrease. With the cobaltic salts for example, it is observed that above a temperature of about $50°$ C, the selectivity of attack at the 2 position of the carbon chain decreases until it becomes practically statistical at approximately $100°$ C. A compromise of these conditions is usually selected. In the majority of cases, a temperature between $20°$ and $50°$ C will advantageously be employed.

The quantity of oxidant to be employed depends on the conversion to be obtained. It is preferred to have low rates of conversion, for example by employing a surplus of substrate with respect to the oxidant to prevent seondary reactions.

The invention is further described with reference to the following Examples.

EXAMPLE 1

This example illustrates the oxidation of n-heptane by an oxidizing system comprising cobaltic acetate and sulphuric acid as an activator. The reaction was performed in the presence of oxygen so as to preferentially produce ketones.

A solution containing 0.50 mol/liter of n-heptane, 0.18 mol/liter of cobaltic acetate and 0.50 mol/liter of sulphuric acid in acetic acid, was stirred at $25°$ C in the presence of pure oxygen at atmospheric pressure. 96% of the cobaltic ions had been reduced after 30 minutes. The reaction mixture was then diluted with a saturated solution of sodium chloride in water, and then repeatedly extracted with ether. The ether extract was neutralized with an aqueous solution of potassium hydroxide and dried over anhydrous sodium sulphate before being analysed by vapor phase chromatography. Analysis showed that 2.6% of the heptane employed had been converted to yield the following oxidation products whose relative proportions are given as molar percentages:

heptanones: 84% (isomer 2:66%; 3:22%; 4:12%)
heptanols: 9% (isomer 1:0%; 2:51%, 3:55%; 4:14%)
heptyl acetates: 7% (isomer 1:0%; 2:70%; 3:30%; 4:traces).

By operating in identical manner, but without adding sulphuric acid to the system, only 0.5% of the cobaltic ions were reduced in 30 minutes. The products formed in these conditions corresponded to a conversion of 0.2% of the heptane employed; that is to say, 13 times smaller than that observed in the presence of sulphuric acid.

EXAMPLE 2

This example illustrates the oxidation of n-heptane by the same oxidizing system as in the preceding example, but this time in the absence of oxygen so as to preferentially produce esters.

The experiment of example 1 was repeated under a nitrogen atmosphere and without stirring. All of the cobaltic ions were reduced after 30 minutes. The analysis of the reaction mixture disclosed the presence of the following oxidation products whose relative proportions are given in molar percentages:

Heptyl acetates: 70% (isomer 1:2%; 2:61%; 3:28%; 4:9%)
Heptanols: 18% (isomer 1:0%; 2:63%; 3:27%; 4:10%)
Heptanones: 12% (isomer 2:62%; 3:31%; 4:7%)

By operating in identical manner but in the absence of the acid activator, no significant decomposition of the cobaltic ions was observed, and no oxidation products were found by analysis.

EXAMPLE 3

The test of example 2 was repeated, but operating at 5° C instead of 25° C, and while continuing the reaction for a total period of two hours. After this time had elapsed, 84% of the cobaltic ions had been reduced, whereas all of these ions had been reduced in 30 minutes in the preceding example. The oxidation products formed in these conditions have the following distribution, in mols:

heptyl acetates: 67% (isomer 1:1%; 2:66%; 3:23%; 4:10%)
heptanones: 25% (isomer 2:65%; 3:24%; 4:11%)
heptanols: 8% (only isomer 2 is detectable)

By comparing these results with those of example 2, it is plain that the reduction in the reaction temperature had caused the latter to slow down, but had also caused a slight improvement in the selectivity of attack on heptane at position 2.

EXAMPLE 4

This example illustrates the oxidation of n-heptane with application of phosphoric acid as an activator, and in the presence of oxygen.

A solution containing 0.50 mol/liter of heptane, 0.18 mol/liter of cobaltic acetate and 1.00 mol/liter of phosphoric acid in acetic acid was stirred at 25° C in the presence of pure oxygen at atmospheric pressure. 38 % of the cobaltic ions was reduced after 60 minutes. The reaction mixture was then treated and analysed as in example 1. Analysis showed that 2.5% of the heptane employed had been converted to yield the following oxidation products whose relative proportions are given as molar percentages:

heptanones: 85% (isomer 2:71%; 3:21%; 4:8%)
heptanols: 15% (isomer 1:0%; 2:75%; 3:25%; 4:traces)

By operating in identical manner, but while omitting the addition of phosphoric acid to the system, only 2% of the cobaltic ions had been reduced after 60 minutes, and the products formed were equivalent to a conversion of not greater than 0.3% of the heptane employed.

EXAMPLE 5

This example illustrates the oxidation of n-heptane by means of the same oxidizing system as in the preceding example, but in the absence of oxygen.

The test of example 4 was repeated under a nitrogen atmosphere and without stirring. 76% of the cobaltic ions were reduced after 60 minutes. Analysis of the reaction mixture disclosed the presence of the following oxidation products whose relative proportions are given as molar percentages:

Heptyl acetates: 86% (isomer 1:1%; 2:71%; 3:21%; 4:7%)
Hepanones: 8% (isomer 2:84%; 3:13%; 4:3%)
Heptanols: 6% (isomer 1:0%; 2:71%; 3:20%; 4:9%)

By operating in identical manner but in the absence of phosphoric acid activator, no reaction of any kind was detectable.

EXAMPLE 6

This example illustrates the oxidation of n-heptane while employing perchloric acid as an activator, and in the absence of oxygen.

A solution containing 0.50 mol/liter of heptane, 0.20 mol/liter of cobaltic acetate and 1.0 mol/liter of perchloric acid in acetic acid was kept at 25° C under a nitrogen atmosphere at atmospheric pressure. The totality of the cobaltic ions was reduced after two hours. The reaction mixture was then treated and analyzed as in example 1. Analysis disclosed the presence of the following oxidation products whose relative proportions are given as molar percentages:

heptyl acetates: 84% (isomer 1:0%; 2:65%; 3:25%; 4:10%)
heptanones: 9% (isomer 2:64%; 3:29%, 4:7%)
heptanols: 7% (isomer 1:0%; 2:36%; 3:465; 4:18%)

EXAMPLE 7

This example illustrates the oxidation of n-heptane with application of boron trifluoride as the activator and in the presence of oxygen.

A solution containing 0.50 mol/liter of heptane, 0.18 mol/liter of cobaltic acetate and 1.50 mol/liter of boron trifluoride in acetic acid was stirred at 25° C in the presence of pure oxygen at atmospheric pressure. 38% of the cobaltic ions were reduced after 18 hours, whereas no reduction of any kind was detectable in a comparative test performed in the absence of the activator. The reaction mixture was then treated and analysed as in example 1. Analysis rendered it possible to identify the following oxidation products whose relative proportions are given as molar percentages:

heptanones: 71% (isomer 2:58%; 3:29%; 4:13%)
heptyl acetates: 18% (isomer 1:0%; 2:66%; 3:24%; 4:10%)
heptanols: 10% (isomer 1:0%; 2:59%; 3:25%; 4:16%)

EXAMPLE 8

This example illustrates the oxidation of n-heptane with application of p-toluenesulphonic acid as the activator and in the absence of oxygen.

A solution containing 0.50 mol/liter of heptane, 0.18 mol/liter of cobaltic acetate and 0.35 mol/liter of p-toluenesulphonic acid in acetic acid was kept at 25° C. without stirring, under a nitrogen atmosphere at atmospheric pressure. 34% of the cobaltic ions had been reduced after 4 hours. The reaction mixture was then treated and analysed as in example 1. Analysis disclosed the presence of the following oxidation products whose relative proportions are given as molar percentages:

heptyl acetates: 81% (isomer 1:0%; 2:72%; 3:22%; 4:6%)
heptanones: 19% (isomer 2:78%; 3:22%; 4:0%)

EXAMPLE 9

This example illustrates the oxidation of n-heptane with application of trifluoracetic acid as an activator and in the presence of oxygen.

A solution containing 0.50 mol/liter of heptane, 0.18 mol/liter of cobaltic acetate and 1.40 mol/liter of trifluoroacetic acid in acetic acid was stirred at 25° C in the presence of pure oxygen at atmospheric pressure. 32% of the cobaltic ions were reduced after 18 hours. The reaction mixture was then treated and analysed as in example 1. Analysis showed that 2.5% of the heptane employed had been converted to yield the following oxidation products whose relative proportions are given as molar percentages:

heptanones: 82% (isomer 2:78%; 3:15%; 4:7%)
heptanols: 14% (isomer 1:0%; 2:79%; 3:15%; 4:6%)
heptyl acetates: 4%.

EXAMPLE 10

This example illustrates the oxidation of n-heptane by means of the same oxidizing system as in the preceding example, but in the absence of oxygen.

The test of example 9 was repeated under a nitrogen atmosphere and without stirring. 51% of the cobaltic ions were reduced after 18 hours. Analysis of the reactive mixture disclosed the presence of the following oxidation products whose relative proportions are given as molar percentages:

heptyl acetates: 78% (isomer 1:1%; 2:76%; 3:17%; 4:6%)
heptanols: 15% (only isomer 2 is detectable)
heptanones: 7% (only isomer 2 is detectable)

EXAMPLE 11

This example illustrates the oxidation of n-heptane with application of dichloracetic acid as the activator, and in the presence of oxygen.

A solution containing 0.50 mol/liter of heptane 0.18 mol/liter of cobaltic acetate an 1.5 mol/liter of dichloroacetic acid in acetic acid, was stirred at 40° C in the presence of pure oxygen at atmospheric pressure. 36% of the cobaltic ions had been reduced after 6 hours. The reaction mixture was then treated and analysed as in example 1. Analysis showed that 3.0% of the heptane employed had been converted to yield the following oxidation products whose relative proportions are given as molar percentages:

heptanones: 80% (isomer 2:83%; 3:12%; 4:5%)
heptanols: 19% (isomer 1:0%; 2:79%; 3:17%; 4:4%)
heptyl acetates: 1%

EXAMPLE 12

This example illustrates the oxidation of n-heptane with application of trichloroacetic acid as the activator and in the presence of oxygen.

A solution containing 0.50 mol/liter of heptane, 0.18 mol/liter of cobaltic acetate and 1.50 mol/liter of trichloroacetic acid in acetic acid, was stirred at 25° C in the presence of pure oxygen at atmospheric pressure. 44% of the cobaltic ions had been reduced after 6 hours. The reaction mixture was then treated and analysed as in example 1. Analysis showed that 4.3% of the heptane had been converted to yield the following oxidation products whose relative proportions are given as molar percentages:

heptanones: 79% (isomer 2:82%; 3:13%; 4:5%)
heptanols: 20% (isomer 1:0%; 2:77%; 3:17%; 4:6%)
heptyl acetates: 1%

EXAMPLE 13

The test of example 12 was repeated but operating at 40° C instead of 25° C. 66% of the cobaltic ions had been reduced after 6 hours. The products formed corresponded to 4.9% of the heptane employed and their relative proportions given as molar percentages, are the following:

heptanones: 84% (isomer 2:79%; 3:15%; 4.6%)
heptanols: 12% (isomer 1:0%; 2:79%; 3:16%; 4:5%)
heptyl acetates: 4%

Compared to the results of example 12, it is apparent that the proportion of heptanones had been increased without serious impairment of selectivity.

EXAMPLE 14

The test of example 13 was repeated, but operating under an oxygen pressure of 10 kgs/em². The oxidation products formed in these conditions were distributed in the following manner, in mols:

heptanones: 83% (isomer 2:79%; 3:15%; 4:6%)
heptanols: 14% (isomer 1:0%; 2.85%; 3.15%; 4:traces)
heptyl acetates: 3%

It is apparent that these results are practically identical to those obtained in example 13. Analogously, no improvement in the proportion of heptanones was observed when the test was performed under an oxygen pressure of 30 kgs/cm².

EXAMPLE 15

This example illustrates the action of temperature on the selectivity of the oxidation of n-heptane at position 2.

A solution containing 0.50 mol/liter of heptane, 0.18 mol/liter of cobaltic acetate and 1.50 mol/liter of trichloroacetic acid in acetic acid was stirred for 4 hours at different temperatures under a pressure of pure oxygen of 10 kgs/cm². After cooling, the reaction mixtures were treated and analysed as in example 1.

Among the oxidation products, analysis detects a preponderance of heptanones whose isomeric distribution is given in the following table:

| Temperature (° C) | Heptanones (%. relative) | | |
|---|---|---|---|
| | 2 | 3 | 4 |
| 25 | 78 | 15 | 7 |
| 40 | 76 | 17 | 7 |
| 60 | 66 | 23 | 11 |
| 80 | 59 | 28 | 13 |

| -continued | | | |
|---|---|---|---|
| Temperature | Heptanones (%. relative) | | |
| 100 | 47 | 36 | 17 |

These results confirm that at 40° C, the proportion of 2-heptanone is practically identical to that observed at 25° C, but that beyond 40° C, it decreases rapidly to approach the statistical value at approximatley 100° C (40% if the terminal methyl groups are ignored).

EXAMPLE 16

This example illustrates the application of propionic acid as a solvent.

A solution containing 0.50 mol/liter of heptane, 0.18 mol/liter of cobaltic acetate and 1.50 mol/liter of trichloroacetic acid in propionic acid, was stirred at 25° C in the presence of pure oxygen at atmospheric pressure.

30% of the cobaltic ions had been reduced after 18 hours. The reaction mixture was then treated and analysed as in example 1. Analysis disclosed the presence of the following oxidation products whose relative proportions are given as molar percentages:
  heptanones: 81% (isomer 2:79%; 3:15%; 4:6%)
  heptanols: 19% (isomer 1:0%; 2:86%; 3:14%; 4:traces)

EXAMPLE 17

Example 16 was repeated, the cobaltic acetate having been replaced by cobaltic propionate.

The results obtained were identical to those of example 16.

EXAMPLE 18

This example illustrates the application of methyl acetate as a solvent.

The test of example 16 was repeated, the propionic acid having been replaced with methyl acetate. The totality of the cobaltic ions was reduced after 18 hours. The reactive mixture was then treated and analysed as in example 1. Analysis disclosed the presence of the following oxidation products whose relative proportions are given as molar percentages:
  heptanones: 77% (isomer 2:84%; 3:12%; 4:4%)
  heptanols: 23% (only isomer 2 is detectable)

EXAMPLE 19

This example illustrates the possiblity of not employing any solvent.

A solution containing 0.18 mol/liter of cobaltic acetate and 1.50 mol/liter of trichloroacetic acid in heptane was stirred at 25° C in the presence of pure oxygen at atmospheric pressure. 47% of the cobaltic ions was reduced after 18 hours. The reaction mixture was then treated and analysed as in example 1. Analysis disclosed the presence of the following oxidation products whose relative proportions are given as molar percentages:
  heptanones: 75% (isomer 2:75%; 3:18%; 4:7%)
  heptanols: 25% (isomer 1:0%; 2:79%; 3:17%; 4:4%)

EXAMPLE 20

This example illustrates the oxidation of n-heptane in the absence of oxygen, by the oxidizing system comprising lead (IV) oxide and sulphuric acid.

A solution containing 0.50 mol/liter of heptane, 0.20 mol/liter of $PbO_2$ and 0.50 mol/liter of sulphuric acid in acetic acid, was kept at 40° C without stirring, under a nitrogen atmosphere at atmospheric pressure. After 24 hours, the reaction mixture was treated in an extraction process analogous to that described in example 1. Analysis of the ether extract disclosed the presence of the following oxidation products whose relative proportions are given as molar percentages:
  heptyl acetates: 93% (isomer 1:0%; 2:59%; 3:28%; 4:13%)
  heptanones: 7% (only isomer 2 is detectable)

EXAMPLE 21

This example illustrates the oxidation of n-heptane in the presence of oxygen, by the oxidizing system comprising silver (II) oxide and trichloroacetic acid.

A solution containing 0.50 mol/liter of n-heptane, 0.20 mol/liter of AgO and 1.50 mol/liter of trichloroacetic acid in acetic acid, was stirred at 40° C in the presence of pure oxygen at atmospheric pressure. After 4 hours, the reactive mixture was treated by an extraction process analogous to that described in example 1. Analysis of the ether extract disclosed the presence of the following oxidation products whose relative proportions are given as molar percentages:
  heptanones: 77% (isomer 2:50%; 3:36%; 4:14%)
  heptanols: 17% (isomer 1:0%; 2:75%; 3:18%; 4:7%)
  heptyl acetates: 6% (only isomer 2 is detectable)

EXAMPLE 22

This example illustrates the oxidation of n-heptane in the absence of oxygen, by means of the oxidizing system comprising ceri-ammonic nitrate and perchloric acid.

A solution containing 0.30 mol/liter of heptane, 0.21 mol/liter of $2NH_4NO_3$. $Ce(NO_3)_4$ and 1.50 mol/liter of perchloric acid in acetic acid was kept at 40° C under a nitrogen atmosphere at atmospheric pressure. After 24 hours, the reaction mixture was treated and analysed as in example 1. A preponderance of heptyl acetates (isomer 1:0%; 2:54%; 3:32%; 4:14%) was detected by analysis, among the products formed.

This example illustrates the oxidation of n-heptane by the oxidizing system comprising chromic anhydride and sulphuric acid.

A solution containing 0.97 mol/liter of heptane, 0.12 mol/liter of $CrO_3$ and 0.05 mol/liter of Sulphuric acid in a mixed solvent of acetic acid and acetic anhydride (50/50 by volume) was kept at 22° C without stirring. 78% of the chromic ions was reduced after 17 minutes. The reaction mixture was then treated and analysed as in example 1. Analysis disclosed the presence of the following oxidation products whose relative proportions are given as molar percentages :
  heptanones: 95% (isomer 2:50%; 3:32%; 4:18%)
  heptanols: 3%
  heptyl acetates: 2%

EXAMPLE 24

This example illustrates the oxidation of n-heptane by the oxidizing system comprising vanadium pentoxide and sulphuric acid.

A solution containing 1.14 mol/liter of heptane, 0.03 mol/liter of $V_2O_5$ and 0.25 mol/liter of sulphuric acid in acetic acid was kept at 75° C, without stirring. 20% of the vanadic ions was reduced after 18 hours. The reaction mixture is then treated and analysed as in example 1. The products detected by analysis were formed almost exclusively by heptyl acetates (isomer 1:0%; 2:56%; 3:31%; 4:13%)

EXAMPLE 25

This example illustrates the oxidation of n-decane in the presence of oxygen, by the oxidizing system comprising cobaltic acetate and trichloroacetic acid.

A solution containing 0.50 mol/liter of decane, 0.18 mol/liter of cobaltic acetate and 1.50 mol/liter of trichloroacetic acid in acetic acid, was stirred at 40° C in the presence of pure oxygen at atmospheric pressure. 71% of the cobaltic ions was reduced after 6 hours. The reaction mixture was then treated and analysed as in example 1.

Analysis shows that 6.2% of the decane employed had been converted to yield the following oxidation products whose relative proportions are given as molar percentages:

decanones: 81% (isomer 2:67%; 3:13%; 4 + 5:20%)
 decanols: 17% (isomer 1:0%; 2:6%; 3:15%; 4 + 5:24%)
 decyl acetates: 2%

This example shows that the selectivity of the process for the position 2 of the carbon chain is equally confirmed in the case of decane, since a statistical attack on the methylene groups of the same should result in no more than 25% of the isomer 2.

EXAMPLE 26

This example illustrates the oxidation of n-decane in the absence of oxygen, by the oxidizing system comprising cobaltic acetate and sulphuric acid.

A solution containing 0.23 mol/liter of decane, 0.20 mol/liter of cobaltic acetate and 0.50 mol/liter of sulphuric acid in acetic acid, was kept at 25° C under a nitrogen atmosphere at atmospheric pressure. 95% of the cobaltic ions was reduced after 30 minutes. The reaction mixture was then treated and analysed as in example 1. Analysis disclosed the presence of the following oxidation products whose relative proportions are given as molar percentages:

decyl acetates: 63% (isomer 1:0%; 2:48%; 3:20%; 4 + 5:32%)
 decanones: 20% (isomer 2:50%; 3:21%; 4 + 5:29%)
 decanols: 17% (isomer 1:0%; 2:29; 3:31%; 4 + 5:40%)

EXAMPLE 27

This example illustrates the oxidation of n-dodecane in the presence of oxygen by the oxidizing system comprising cobaltic acetate and trichloroacetic acid.

By proceeding with dodecane in a manner wholly identical to that applied in example 25, it was determined that 5.9% of the dodecane employed had been converted to yield the following oxidation products whose relative proportions are given as molar percentages:

dodecanones: 78% (isomer 2:65%; 3:13%; 4 + 5:22%; 6:0%)
 dodecanols: 20% (isomer 1:0%; 2:51%; 3:15%; 4 + 5:34%; 6:0%)
 dedecyl acetates: 2%.

It should be noted that a statistical attack on the methylene groups of dodecane would result in no more than 20% of the isomer 2.

As thus described a straight chain paraffin hydrocarbon of any chain length up to 60 usually in the range of 3 to 20 may be oxidized to introduce an oxygenated function into the chain such as carbinol, esters thereof and ketone, predominately in the 2 position. The oxidation is effected by a multivalent metal compound of groups II - VI of the periodic table used in a higher valency state, the metal having an oxidation reduction potential of at least 0.99 volt. The metal compound is usually an oxide or salt, preferably of a lower fatty acid of up to 4 carbon atoms. The reaction is effected in the presence of a strong acid having a dissociation constant exceeding $5.10^{-3}$ or/and acid acting substances such as boron trifluoride, stable to the oxidizing conditions of the system. The reaction may be run in the presence of a solvent which is also stable to the oxidizing system; for example, lower fatty acids having 1 – 4 carbon atoms and methyl or tertiary butyl esters thereof.

What is claimed is:

1. Process for the selective oxidation of straight chain paraffin hydrocarbons having 3 to 60 carbon atoms into oxygenated products having the same number of carbon atoms comprising predominantly saturated ketones wherein the oxygenated function is predominantly located in the 2-position, comprising reacting said hydrocarbon in a liquid phase free of oxidizable solvent in an atmosphere comprising free oxygen with an oxidizing system consisting essentially of oxides and salts of a metal of variable valency of group II though VI and cobalt, the metal in said compound being in its higher valency state and having an oxidation-reduction potential of at least 0.99 volts, and an activator selected from the group consisting of boron trifluoride and strong stable organic and inorganic acids having a dissociation constant greater than $5 \cdot 10^{-3}$, selected from the group consisting of sulfuric, phosphoric, perchloric, dichloracetic, trichloracetic, trifluoracetic, and p-toluenesulfonic and mixtures thereof, at a temperature in the range of $-20°$ C to $+80°$ C.

2. The process for the selective oxidation of straight paraffin hydrocarbons having 3 to 60 carbon atoms into oxygenated products having the same number of carbon atoms comprising predominantly saturated ketones wherein the oxygenated function is predominantly located on the 2-position of the carbon chain, comprising said hydrocarbon in the presence of a solvent stable to oxidation under the reaction conditions and selected from the group consisting of methyl and tertiarybutyl esters of lower fatty acids having 1 to 4 carbon atoms in the presence of free oxygen, with an oxidizing system cnsisting of oxides and salts of a metal of variable valency of group II through VI and cobalt, the metal in said compound being in its higher valency state and having an oxidation-reduction potential of at least 0.99 volt, and an activator selected from the group consisting of boron trifluoride and strong stable organic and inorganic acids, having a dissociation constant greater than $5 \cdot 10^{-3}$, of the group consisting of sulfuric, phosphoric, perchloric, dichloracetic, trichloracetic, and p-toluenesulfonic and mixtures thereof, at a temperature in the range of $-20°$ C to $+50°$ C.

3. A process for the selective oxidation of straight chain paraffins having 3 to 20 carbon atoms predominantly into saturated ketones having the same number of carbon atoms, wherein the oxygenated function is predominantly located on position 2 of the carbon chain as defined in claim 1 wherein the oxidizing system comprises a cobaltic salt as the catalyst, at a temperature between $-20°$ C and $+50°$ C and under an oxygen partial pressure between 0.1 and 50 atmospheres.

4. A process for the selective oxidation of straight chain paraffins having from 3 to 20 carbon atoms predominantly into saturated ketones having the same number of carbon atoms, wherein the oxygenated function is predominantly located on position 2 of the carbon chain as defined in claim 1 wherein the oxidizing system comprises a cobaltic salt of a fatty acid having from 2 to 4 carbon atoms as the catalyst, at a temperature between −20° C and +50° C, and under an oxygen partial pressure between 0.1 and 50 atmospheres.

5. The process as defined in claim 1 wherein the solvent is selected from the group consisting of fatty acids having from 2 to 4 carbon atoms and their methyl esters and the temperature of the reaction in the range of −20° C to +50° C.

6. The process as defined in claim 5 wherein the solvent is acetic acid.

7. The process as defined in claim 1 wherein the cobaltic salt is cobaltic acetate.

* * * * *